United States Patent
Shimano et al.

(10) Patent No.: US 8,697,749 B2
(45) Date of Patent: Apr. 15, 2014

(54) LIPOTOXICITY RELIEVING AGENT

(75) Inventors: Hitoshi Shimano, Ibaraki (JP); Toyonori Kato, Shizuoka (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 771 days.

(21) Appl. No.: 12/431,668

(22) Filed: Apr. 28, 2009

(65) Prior Publication Data

US 2009/0209644 A1  Aug. 20, 2009

Related U.S. Application Data

(62) Division of application No. 11/794,697, filed as application No. PCT/JP2006/300008 on Jan. 4, 2006, now abandoned.

(30) Foreign Application Priority Data

Jan. 4, 2005 (JP) .............................. 2005-000168

(51) Int. Cl.
*A61K 31/202* (2006.01)
*A23D 9/00* (2006.01)

(52) U.S. Cl.
USPC .......................................... 514/560; 554/224

(58) Field of Classification Search
None
See application file for complete search history.

(56) References Cited

FOREIGN PATENT DOCUMENTS

WO   WO-2004/078166   9/2004

OTHER PUBLICATIONS

Nobukata et al., "Long-Term Administration of Highly Purified Eicosapentaenoic Acid Ethyl Ester Prevents Diabetes and Abnormalities of Blood Coagulation in Male WBN/Kob Rats," Metabolism, vol. 49, No. 7, Jul. 2000: pp. 912-919.*
Gregorio et al., "Therapeutical concentrations of tolbutamide, glibenclamide, glicazide and gliquidone at different glucose levels: in vitro effects on pancreatic A- and B-cell function," Diabetes Research and Clinical Practice, 18(3), Dec. 1992, pp. 197-206—abstract only.*
Unger, R., "Lipotoxic Diseases," Annu. Rev. Med., 2002, vol. 53, pp. 319-336.
Listenberger et al., "Triglyceride accumulation protects against fatty acid-induced lipotoxicity," PNAS, vol. 100, No. 6, Mar. 18, 2003, pp. 3077-3082.
European Office Action dated Jul. 20, 2009 for corresponding European Application No. 06702028.9.
Itoh Y. et al., Nature, 2003, vol. 422, No. 6928, pp. 173 to 176.
Woodman, R.J. et al., American Journal of Clinical Nutrition, 2002, vol. 76, No. 5, pp. 1007 to 1015.
Opara, E.C. et al., Endocrinology, 1992, vol. 130, No. 2, pp. 657 to 662.
Eto, K. et al., Diabetes, 2002, vol. 51, no. Suppl. 3, pp. 414 to 420.
Hiroshi Hirose, The Cell, 2001, vol. 33, No. 8, pp. 302 to 305.
Maedler, K. et al., Diabetes, 2001, vol. 50, pp. 69-76.
Maedler, K. et al., Diabetes, 2003, vol. 52, pp. 726-733.
Eitel, KI., Biochemical and Biophysical Research Communications, 2002, vol. 299, pp. 853-856.
Busch, A. N. et al., Diabetes, 2002, vol. 51, pp. 977-987.
Schaffer, Jean E., Lipotoxicity: when tissues overeat, Current Opinion in Lipidology, 2003, 14, pp. 281-283.
Communication pursuant to Article 94(3) EPC issued Feb. 13, 2012, in European Patent Application No. 06 702 028.9.
Pighin et al., "Fish Oil Affects Pancreatic Fat Storage, Pyruvate Dehydrogenase Complex Activity and Insulin Secretion in Rats Fed a Sucrose-Rich Diet," J. Nutr. (2003), vol. 133, pp. 4095-4101.
International Search Report for PCT/JP2006/300008 mailed Feb. 14, 2006.
Partial English translation of "Shimabukuro Sensei, '5. Yuri Shibosan no. Seiri Kassei: Shobo Dokusei no Kiso to Rinsho,' 2003, pp. 24-29,".
Sharma et al., "Intramyocardial Lipid Accumulation in the Failing Human Heart Resembles the Lipotoxic Rat Heart" pp. 1692-1700. The FASEB Journal, vol. 18, Nov. 2004.
Gosh et al., "Role of Dietary Fatty Acids and Acute Hyperglycemia in Modulating Cardiac Cell Death" pp. 916-923. Nutrition, vol. 20, No. 10, 2004.

* cited by examiner

*Primary Examiner* — Sreeni Padmanabhan
*Assistant Examiner* — Jody Karol
(74) *Attorney, Agent, or Firm* — Birch, Stewart, Kolasch & Birch, LLP

(57) ABSTRACT

In view of the situation that a clinically acceptable medical agent which has the action of preventing and relieving the lipotoxicity with no significant side effects is not yet provided, such medical agent is provided. An agent for relieving lipotoxicity which comprises an unsaturated fatty acid containing 18 to 22 carbon atoms and having a degree of unsaturation of 3 to 6 or a derivative thereof as its effective component.

17 Claims, 5 Drawing Sheets

LIPOTOXICITY RELIEVING AGENT

CROSS-REFERENCE TO A RELATED APPLICATION

This application is a 37 C.F.R. §1.53(b) divisional of co-pending application Ser. No. 11/794,697, filed on Jul. 3, 2007, which claims priority on PCT/JP06/300008 filed on Jan. 4, 2006, which in turn claims priority on Japanese Application No. 2005-000168, filed on Jan. 4, 2005. The entire contents of each of these applications is hereby incorporated by reference.

BACKGROUND OF THE INVENTION

1. Field of the Invention

This invention relates to an agent for relieving lipotoxicity.

2. Description of the Related Art

Adipocyte is a cell which is specialized in storing a large amount of free fatty acid as neutral fat, and cells other than adipocyte (nonadipocyte) are incapable of storing such a large amount of neutral fat. In the adipocyte, neutral fat is decomposed into diacylglycerol and a free fatty acid either continuously or in response to the particular stimulus. Although a free fatty acid is a hemolysin toxin which is insoluble in water, it becomes soluble and non-toxic by binding to albumin, and the fatty acid-albumin complex is carried to liver where it is consumed. When the fatty acid-albumin complex enters the liver, the fatty acid is quickly incorporated by the liver, and only the albumin returns to the blood. The free fatty acid caused by degradation is re-esterified by the action of insulin. As a consequence of such mechanism, concentration of the free fatty acid in plasma is maintained under normal conditions within a certain range.

However, when a large amount of free fatty acid is continuously present in the plasma (hyper-free fatty acidemia) for some reasons, for example, by continuous lipolysis under the reduced action of insulin, dysfunction of nonadipocyte of liver, heart, pancreas, kidney, skeletal muscle, and the like is sometimes generated by the re-distribution of the free fatty acid, and this dysfunction is called "lipotoxicity".

When the nonadipocyte is pancreatic β-cell, the lipotoxicity is known to induce apoptosis and impairment of glucose-stimulated insulin secretion. More specifically, there has been reported that palmitic acid induces β-cell apoptosis, decrease β-cell prolification, and impairment of glucose-stimulated insulin secretion of the cultivated pancreatic β-cell, and stearic acid induces apoptosis of the cultivated pancreatic β-cell (see, for example, Non-patent documents 1 to 3).

The decrease of the glucose-stimulated insulin secretion in the pancreatic β-cell results in the increase of blood glucose level.

It has also been known that chronic high blood glucose level higher than the normal level may result in the dysfunction of the pancreatic β-cell, and this dysfunction is called glucotoxicity. More specifically, this glucotoxicity is known to induce increase in glucose sensitivity of the pancreatic β-cell to invite excessive secretion of the insulin, and this results in the exhaustion of the pancreatic β-cell and decrease of the glucose-stimulated insulin secretion. Decrease in the number of the pancreatic β-cell is also known to occur (see, for example, Non-patent document 2).

This results in the vicious circle that the increase in the blood glucose level caused by the lipotoxicity induces the glucotoxicity while decrease in the insulin action induces the lipotoxicity, and this vicious circle promotes progress from abnormal glucose tolerance to diabetes in the patients of abnormal glucose tolerance, as well as worsening of the conditions in the diabetes patients.

In the experiments carried out by using rat and human cultivated pancreatic β-cells, some fatty acids, for example, palmitoleic acid (an ω7 fatty acid containing 16 carbon atoms and having a degree of unsaturation of 1), oleic acid (an ω9 fatty acid containing 18 carbon atoms and having a degree of unsaturation of 1), and linoleic acid (an ω6 fatty acid containing 18 carbon atoms and having a degree of unsaturation of 2) have been reported to exhibit action of preventing lipotoxicity and glucotoxicity.

It has also been disclosed that, β-cell apoptosis, decrease β-cell prolification, and suppression of the glucose-stimulated insulin secretion of the pancreatic β-cell are counteracted by preliminary addition of palmitoleic acid to the lipotoxicity induced by palmitic acid (a saturated fatty acid) in the Langerhans cell of rat pancreas (see, for example, Non-patent document 1).

Similarly, there is a disclosure that β-cell apoptosis, decrease β-cell prolification, and suppression of the glucose-stimulated insulin secretion of the cultivated pancreatic β-cell are counteracted by preliminary addition of palmitoleic acid or oleic acid to the lipotoxicity induced by palmitic acid and/or glucotoxicity induced by glucose in the Langerhans cell of human pancreas (see, for example, Non-patent document 2).

It has also been disclosed that apoptosis of the pancreatic β-cell was suppressed by the preliminary addition of palmitoleic acid, oleic acid, or linoleic acid to the lipotoxicity induced by palmitic acid in the cultivated Langerhans cell of human and rat pancreas (see, for example, Non-patent document 3).

In the meanwhile, oleic acid has also been reported to induce decrease of the glucose-stimulated insulin secretion in rat cultivated pancreatic β-cell to further induce the lipotoxicity (see, for example, Non-patent document 4). These publications disclose results of experiments carried out by using cultivated cells on the action of several fatty acids in preventing the lipotoxicity and/or the glucotoxicity. However, these results include contradictory results as in the case of oleic acid, and the situation is not necessarily clear. In addition, there is no disclosure indicative of the in vivo action, the relieving action, or a substance having both the preventive and relieving actions.

Thiazolidine derivatives are known to have the action of protecting the nonadipocyte by accumulating the free fatty acid in the adipocyte, and biguanide drugs are known to normalize sugar usage and oxidation in the pancreatic β-cell which had been damaged by the lipotoxicity. Nicotinamide and aminoguanidine which are inhibitors of inducible nitric oxide synthase (iNOS) have been indicated to have the possibility of suppressing the apoptosis induced by the lipotoxicity. These drugs, however, are known to have side effects. As described above, there is so far no clinically acceptable drug that has the action of relieving the lipotoxicity, and hence, the action of relieving the glucotoxicity, as well as the reduced side effects.

Non-patent document 1: Maedler, K. et al., Diabetes, 2001, vol. 50, pp. 69-76
Non-patent document 2: Maedler, K. et al., Diabetes, 2003, vol. 52, pp. 726-733
Non-patent document 3: Eitel, K., Biochemical and Biophysical Research Communications, 2002, vol. 299, pp.
Non-patent document 4: Busch, A. N. et al., Diabetes, 2002, vol. 51, pp. 977-987

DISCLOSURE OF THE INVENTION

Problems to be Solved by the Invention

An object of the present invention is to provide a clinically acceptable medicament which has the prophylactic and relieving action against the lipotoxicity with no significant side effects in view of the situation that such drug is not yet provided.

Means to Solve the Problems

The inventors of the present invention made an intensive study to solve the problems as described above, and found that an unsaturated fatty acid containing 18 to 22 carbon atoms and having a degree of unsaturation of 3 to 6 and derivatives thereof have the prophylactic and relieving effect against the lipotoxicity. The present invention has been completed on the basis of such finding. Accordingly, the present invention provides:

(1) An agent for relieving lipotoxicity which comprises an unsaturated fatty acid containing 18 to 22 carbon atoms and having a degree of unsaturation of 3 to 6 or a derivative thereof or mixture thereof as its effective component.

Specifically, (2) The lipotoxicity relieving agent according to (1) wherein the lipotoxicity is dysfunction of pancreatic β-cell.

(3) The lipotoxicity relieving agent according to (2) wherein the dysfunction of the pancreatic β-cell is impaired insulin secretion.

(4) The lipotoxicity relieving agent according to (2) wherein the dysfunction of the pancreatic β-cell is impaired cell death.

In specific embodiments, (5) The lipotoxicity relieving agent according to any one of (1) to (4) wherein the unsaturated fatty acid is a ω3 fatty acid or its derivative.

(6) The lipotoxicity relieving agent according to (5) wherein the unsaturated fatty acid is at least one member selected from α-linolenic acid, icosapentaenoic acid, docosahexaenoic acid, and derivatives thereof.

(7) The lipotoxicity relieving agent according to (6) wherein the derivative of an unsaturated fatty acid is ethyl icosapentate and/or ethyl docosahexaenoate.

More specifically, (8) The lipotoxicity relieving agent according to any one of (1) to (7) wherein the lipotoxicity relieving agent is administered to a hyper-free fatty acidemia patient.

(9) a method for preventing and relieving pathological conditions by administering the lipotoxicity relieving agent according to any one of (1) to (8).

(10) Use of an unsaturated fatty acid containing any of 18 to 22 carbon atoms and having any degree of unsaturation of 3 to 6 or a derivative thereof for manufacturing the lipotoxicity relieving agent according to any one of (1) to (8).

Effects of the Invention

The lipotoxicity relieving agent of the present invention comprising the unsaturated fatty acid containing 18 to 22 carbon atoms and having a degree of unsaturation of 3 to 6 or a derivative thereof as its effective component as described above is useful as a medicament for preventing and relieving the lipotoxicity in various causes, diseases, and pathologic conditions.

BRIEF DESCRIPTION OF THE DRAWINGS

FIG. 1 shows insulin secretion per mg of the protein when Min6 cells of various groups are stimulated with glucose.

FIG. 2 shows insulin secretion per mg of the protein when various fatty acids are added to the Min6 cells under the load of palmitic acid and the cells are further stimulated with glucose.

BEST MODE FOR CARRYING OUT THE INVENTION

Figure 1:
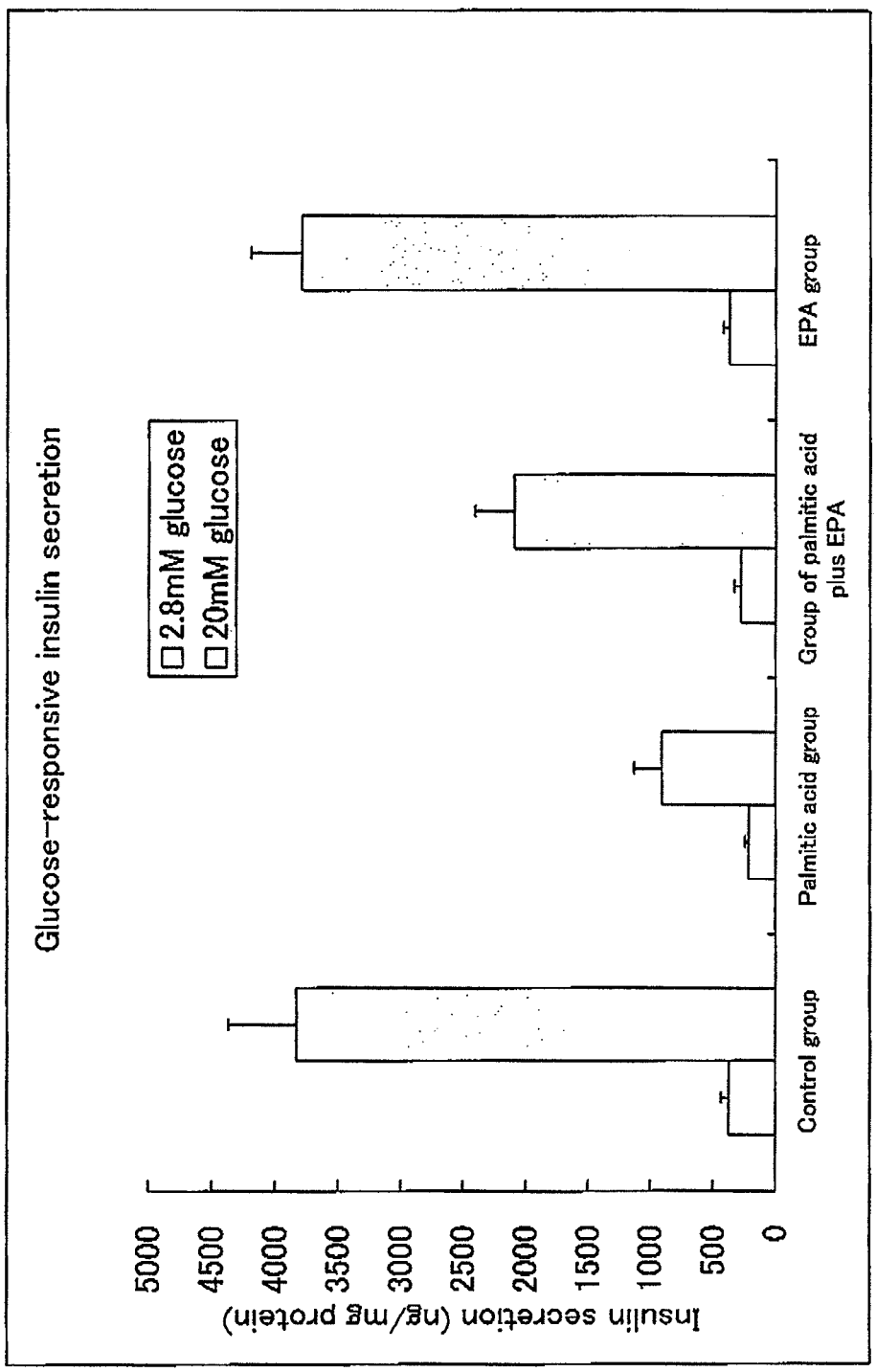
FIG. 1 is a graph showing the effect of the lipotoxicity relieving agent of the present invention in inhibiting (prophylactic effect) the impaired insulin secretion of the pancreatic β-cell induced by the lipotoxicity. More specifically.

Next, the present invention is described in detail.

The present invention relates to an agent for relieving lipotoxicity comprising an unsaturated fatty acid containing 18 to 22 carbon atoms and having a degree of unsaturation of 3 to 6 or a derivative thereof (hereinafter sometimes generally referred to as the particular unsaturated fatty acid) as its effective component. In the present invention, the term "agent for relieving lipotoxicity" or "lipotoxicity relieving agent" also includes an agent for preventing the lipotoxicity.

Exemplary derivatives of the unsaturated fatty acid include a salt with an inorganic base such as sodium salt, a salt with an organic base such as benzylamine salt, a salt with a basic amino acid, and an ester such as an alkylester (for example, ethyl ester) or glyceride. The more preferred are triglycerides and ethyl esters, and the preferred is an ethyl ester.

In the present invention, the preferable examples of the particular unsaturated fatty acid are ω3 fatty acids and their derivatives.

Preferable examples of such unsaturated fatty acid include at least one member selected from α-linolenic acid (hereinafter abbreviated as αLA), eicosapentaenoic acid (hereinafter abbreviated as EPA), docosahexaenoic acid (hereinafter abbreviated as DHA), and their derivatives.

EPA is an unsaturated fatty acid containing 20 carbon atoms and having a degree of unsaturation of 5. The EPA used in the present invention is a straight chain unsaturated ω3 fatty acid having double bonds at positions 5, 8, 11, 14, and 17, which are all cis. DHA is an unsaturated fatty acid containing 22 carbon atoms and having a degree of unsaturation of 6. The DHA used in the present invention is a straight chain unsaturated ω3 fatty acid having double bonds at positions 4, 7, 10, 13, 16, and 19, which are all cis. αLA is an unsaturated fatty acid containing 18 carbon atoms and having a degree of unsaturation of 3. More specifically, αLA is a straight chain unsaturated ω3 fatty acid having double bonds at positions 9, 12, and 15, which are all cis.

The preferred embodiments of derivatives in such preferable unsaturated fatty acids are the same as those described above.

Exemplary preferred embodiments are the lipotoxicity relieving agent wherein the derivative of the unsaturated fatty acid includes an EPA ethyl ester (hereinafter abbreviated as an EPA-E) and/or a DHA ethyl ester (hereinafter abbreviated as a DHA-E) as its effective component.

The present invention provides a lipotoxicity relieving agent which contains the particular unsaturated fatty acid as described above as its effective component.

The "lipotoxicity" in the present invention means dysfunction of nonadipocytes of liver, heart, pancreas, kidney, skeletal muscle, and the like induced when a large amount of free fatty acids are continuously or repetitively present in plasma, and in particular in portal vein plasma for some reasons. When the nonadipocyte is pancreatic β-cell, the lipotoxicity will be induction of pancreatic β-cell apoptosis, decrease β-cell prolification, and impairment of glucose-stimulated insulin secretion of the pancreatic β-cell. In addition, the decrease in the glucose-stimulated insulin secretion of the pancreatic β-cell invites increase in the blood glucose level.

Typical fatty acids that causes lipotoxicity include palmitic acid, stearic acid, and oleic acid. The fatty acid, however, is not limited to such fatty acids.

Accordingly, an embodiment of the present invention is a lipotoxicity relieving agent wherein the lipotoxicity is dysfunction of the pancreatic β-cell.

The pancreatic β-cell is an insulin-secreting cell found in Langerhans' islet of pancreas. Proinsulin, which is the precursor for the insulin is biosynthesized in rough-surfaced endoplasmic reticulum of the pancreatic β-cell, and after its conversion into the insulin, the insulin stored in the pancreatic β-cell is released into blood in response to secretion stimulus. The secretion is mainly promoted by glucose. One main physiologic action of insulin is hypoglycemic action. Typical dysfunctions of the pancreatic β-cell include impaired insulin secretion, suppression of proliferation, and cell death (necrosis and apoptosis).

More specifically, the present invention provides a lipotoxicity relieving agent wherein the dysfunction of the pancreatic β-cell is impaired insulin secretion.

Even more specifically, the present invention provides a lipotoxicity relieving agent wherein the dysfunction of the pancreatic β-cell is cell death. In the present invention, the cell death includes both the necrosis and the apoptosis.

The lipotoxicity relieving agent of the present invention is typically administered to patients suffering from hyper-free fatty acidemia. Hyper-free fatty acidemia is a condition in which a large amount of free fatty acid is continuously or repetitively present in plasma, and in particular, in portal vein plasma. Hyper-free fatty acidemia may induce dysfunction of nonadipocytes, namely, the lipotoxicity.

The lipotoxicity relieving agent of the present invention contains at least one of the particular unsaturated fatty acids described above as its effective component, which may be the particular unsaturated fatty acid used alone or in combination or two or more.

Content of the unsaturated fatty acid which is the effective component of the lipotoxicity relieving agent of the present invention is not particularly limited. The content, however, is preferably 20% by weight or more, more preferably 50% by weight or more, still more preferably 85% by weight or more, and still more preferably 95% by weight or more in relation to the weight of total fatty acid content, and most preferably, the lipotoxicity relieving agent is substantially free from fatty acid components other than the unsaturated fatty acid.

The effective component of the lipotoxicity relieving agent of the present invention is preferably a ω3 polyunsaturated fatty acid, and in particular, EPA and/or DHA, and as the derivatives of the ω3 polyunsaturated fatty acid, the preferred is EPA-E and/or DHA-E.

The unsaturated fatty acid used in the lipotoxicity relieving agent of the present invention may be prepared by a method known in the art such as extraction and purification from a natural matter or chemical synthesis. The method used in the esterification of the resulting unsaturated fatty acid is known to those skilled in the art.

The lipotoxicity relieving agent used in the present invention is preferably a naturally occurring unsaturated fatty acid. More specifically, sardine oil, squid oil, cod liver oil, menhaden oil, krill oil, herring oil, saury oil, mackerel oil may be treated by a method known in the art such as deoxidation, decolorization, deodorization, degumming, and dewaxing, optionally followed by solvent fractionation, urea adduct method, molecular distillation, or the like to produce a mixture of EPA and other fatty acids such as DHA concentrated to a certain degree.

The lipotoxicity relieving agent of the present invention may be administered either as the particular unsaturated fatty acid alone, namely, as effective ingredients alone, or by preparing an adequate composition or pharmaceutical formulation by combining the particular unsaturated fatty acid with an adequate vehicle or a medium commonly used in the art such as an excipient, a binder, a lubricant, a colorant, or a flavor; and in some cases, a sterilized water or a vegetable oil; and further in combination with a non-toxic organic solvent or a non-toxic solubilizer (such as glycerin or propylene glycol), an emulsifier, a suspending agent (for example, Tween 80 and gum arabic solution), an isotonizing agent, a pH adjusting agent, a stabilizer, an soothing agent, and the like.

The lipotoxicity relieving agent of the present invention may also contain, as an effective component other than the unsaturated fatty acid and its derivative, an aqueous extract of red grape leaf or the flavonoid which is the effective component of the extract, an extract of the bark of the French maritime pine or pycnogenol which is the effective component of the extract, horse chestnut extract, or hazel extract. It may also contain a component such as lecithin capable of promoting absorption of the unsaturated fatty acid and its derivatives.

The lipotoxicity relieving agent of the present invention is preferably administered in combination with a drug having the action of promoting insulin secretion of pancreatic β-cell, for example, a sulfonylurea insulin secretion promoter such as tolbutamide, glimepiride, gliclazide, or glibenclamide, a rapid acting insulin secretion promoter such as nateglinide or mitiglinide, or a biguanide drug such as metformin or buformin.

In the present invention, the combined administration includes administration of a preparation having the combination of drugs incorporated therein; simultaneous administration of separate preparations; and administration of one preparation followed by the administration of another preparation.

The combined administration is expected to enhance the lipotoxicity relieving action, and also to inhibit progress of the impaired glucose tolerance to the borderline diabetes or the diabetes. The combined administration is also expected to enable decrease of the dose of each drug, number of doses, dosing period and ameliorate the quality of life of the patients, for example, by alleviating the side effects.

The lipotoxicity relieving agent of the present invention is administered to the patient in the dosage form of tablet, capsule, microcapsule, granule, fine granule, powder, liquid preparation for oral administration, jelly, suppository, syrup, inhalant, eye drop, ointment, injection (emulsion, suspension, or non-aqueous), and solid injection which is emulsified or suspended immediately before its use. The lipotoxicity relieving action may be administered to the patient, for example, orally, intravenously, intraarterial, by inhalation, by instillation from eye, intrarectally, intravaginally, or externally. The preferred form is capsule such as soft capsule or microcapsule which is orally administered. Also preferred are an injection (emulsion, suspension, or non-aqueous), and a solid injection which is to be emulsified or suspended immediately before its use for intravenous or intraarterial administration.

EPADEL in the form of a soft capsule and EPADEL S in the form of a seamless capsule both containing high purity EPA-E (both being products manufactured by Mochida Pharmaceutical Co., Ltd.) are commercially available in Japan, and they are highly safe therapeutic agents with reduced side effects used for improvement of ulcer, pain, or cold feeling associated with arteriosclerosis obliterans, and for hyperlipidemia. EPADEL and EPADEL S may be used for the lipotoxicity relieving agent of the present invention.

The lipotoxicity relieving agent of the present invention can be used for preventing and ameliorating lipotoxicity of various causes, diseases, and pathologic conditions. The lipotoxicity relieving agent of the present invention may be administered for the purpose of preventing and ameliorating lipotoxicity in the patients suffering from hyper-free fatty acidemia and in particular, in the patients whose free fatty acid level in portal vein plasma is continuously or repeatedly high associated with obesity, overeating, lack of exercise, and high fat diet, and in particular, Western diet mainly taking animal meats, hyperlipemia, hyperglycemia, abnormal glucose tolerance, hyperinsulinemia, diabetes, hepatic insufficiency, hepatic encephalopathy, liver cirrhosis, jaundice, ascites, hepatitis, pancreatitis, pancreatic dysfunction, renal failure, nephrotic syndrome, nephritis, uremia, cardiac failure, cardiomyopathy, rhabdomyolysis, and the like.

Among such hyperlipemia patients, the lipotoxicity relieving agent of the present invention is particularly suitable for use in preventing and ameliorating the lipotoxicity in those suffering from hypertriglyceridemia, and in particular, postprandial hypertriglyceridemia with repeated transient increase of triglyceride concentration in the plasma after the meal, as well as in the hyperglycemia, abnormal glucose tolerance, borderline diabetes, and diabetes.

The lipotoxicity relieving agent of the present invention is even more adapted for use in the patients suffering from hyper-free fatty acidemia, and in particular, in the patients exhibiting the hyper-free fatty acidemia in portal vein plasma with high concentration of the saturated fatty acid such as palmitic acid and stearic acid or oleic acid and/or with high proportion of the saturated fatty acid such as palmitic acid and stearic acid or oleic acid in the free fatty acids. The lipotoxicity relieving agent has also enabled to set up an administration plan or determining the degree of prophylaxis or amelioration while monitoring such index.

Of the patients as described above exhibiting the hyper-free fatty acidemia which is the disease or pathologic conditions suitable for application of the lipotoxicity relieving agent of the present invention, the lipotoxicity relieving agent of the present invention is most adapted for use in patients exhibiting high concentration of the saturated fatty acid such as palmitic acid and stearic acid or oleic acid and/or the patients exhibiting high proportion of the saturated fatty acid such as palmitic acid and stearic acid or oleic acid in the free fatty acids.

The lipotoxicity relieving agent of the present invention may be administered at any amount sufficient for them to exert the intended effect. The amount, however, may be adjusted as appropriate to reflect the dosage form, administration route, number of doses a day, seriousness of the symptom, body weight, age, and the like. For example, in the case of oral administration of as a lipotoxicity relieving agent, the agent is preferably administered at 0.1 to 9 g/day, preferably 0.5 to 6 g/day, and more preferably 1 to 3 g/day in terms of EPA, and the agent may be administered as appropriate in a single dose or in divided doses, and preferably in several doses, and in particular, in about three divided doses. In the case of oral administration, the agent is administered within 60 minutes after the meal, and preferably immediately after the meal. In the case of intravenous or intraarterial administration, the agent is preferably administered at 1 to 200 mg, preferably 5 to 100 mg, and more preferably 10 to 50 mg in terms of EPA, and the agent may be administered as appropriate in a single dose or in divided doses. Also, if necessary, the agent may be administered continuously for several hours to several days by drip infusion, infusion pump, or the like as desired.

EXAMPLES

Next, the present invention is described in further detail by referring to the Examples which are presented as exemplary embodiments and which by no means limit the scope of the present invention. The abbreviations used in the following description are those based on customary uses in the relevant art. In Experimental Examples 1 and 2, the fatty acids used were sodium salts of the fatty acids (manufactured by Sigma).

Experimental Example 1

Effect of the Long Chain Polyunsaturated Fatty Acid on Inhibition (Prophylaxis) of the Impaired Insulin Secretion of Pancreatic β-Cell Induced by Lipotoxicity (1) Exposure of Min6 Cell to Fatty Acid Min6 cells from mouse pancreatic β-cell (provided by Dr. Miyazaki of Osaka University) suspended in DMEM medium (manufactured by GIBCO, purchased from Iwai Chemicals Company) were seeded in a 24 well plate at 1.5× $10^5$ cells per well, and the cells were incubated in 5% $CO_2$ at 37° C. for 24 hours.

The medium was replaced with DMEM medium (manufactured by Sigma) containing 0.5% (v/v) fatty acid free bovine serum albumin (hereinafter abbreviated as BSA) and 5.5 mM glucose, and incubated in 5% $CO_2$ at 37° C. for 48 hours with or without (control group) one of the following fatty acids, 0.4 mM palmitic acid (palmitic acid group), 50 μM EPA (EPA group), or 0.4 mM palmitic acid and 50 μM EPA (the group of palmitic acid plus EPA).

(2) Measurement of Insulin Secretion

<Stimulation with Glucose>

The supernatant was removed from the cell culture of (1), and the cells were washed twice with phosphate buffered saline (hereinafter abbreviated as PBS(−)), and after adding 500 μL of Krebs-Ringer-Bicarbonate-Hepes buffer (hereinafter abbreviated as KRBH buffer) containing 0.5% (v/v) fatty acid free BSA and 2.8 mM glucose, the incubated was continued in 5% $CO_2$ at 37° C. for 1 hour.

The supernatant was removed from the cell culture, and after adding 500 μL of KRBH buffer containing 0.5% (v/v) BSA and 2.8 mM glucose, the incubation was continued in 5% $CO_2$ at 37° C. for 1 hour, and the supernatant was collected as the sample which had been stimulated with 2.8 mM glucose.

Next, the cells were washed twice with PBS(−), and incubated in KRBH buffer containing 0.5% (v/v) BSA and 20 mM glucose in 5% $CO_2$ at 37° C. for 1 hour. The supernatant was collected as the sample which had been stimulated with 20 mM glucose.

<Measurement>

The samples collected were evaluated for their insulin concentration by Levis insulin assay kit (manufactured by Shibayagi and purchased from Nakayama Co., Ltd.) and for their protein concentration by the method of Lowry (BCA kit), and determine the amount of insulin per mg of the protein. The results are shown in FIG. 1.

No difference was recognized for the insulin secretion of the sample stimulated with 2.8 mM glucose between the groups. With regard to the insulin secretion of the sample stimulated with 20 mM glucose, the insulin secretion was 3836 ng in the control group (assumed to be 100%) whereas it was 910 ng (23.7%) in the palmitic acid group. The insulin secretion was 3664 ng (95.5%) in the EPA group and 2096 ng (54.6%) in the group of palmitic acid plus EPA. As demonstrated by these results, EPA has the effect of inhibition on the impaired insulin secretion induced by lipotoxicity while EPA used alone does not affect the insulin secretion.

Experimental Example 2

Restorative Effect of the Long Chain Polyunsaturated Fatty Acid of the Impaired Insulin Secretion of Pancreatic β-Cell Induced by Lipotoxicity (1) Exposure of Min6 Cell to Fatty Acid
(1-1) Min6 cells suspended in DMEM medium (manufactured by Gibco) were seeded in a 24 well plate at $1.5 \times 10^5$ cells per well, and the cells were incubated overnight in 5% $CO_2$ at 37° C.
(1-2) To each well, palmitic acid was added to a concentration of 0.4 mM, and BSA not containing the fatty acid was added to a concentration of 0.5% (v/v), and the incubation was continued in 5% $CO_2$ at 37° C. for 48 hours.
(1-3) The cells were washed twice with PBS(−), and the incubation was continued in 5% $CO_2$ at 37° C. for 48 hours in DMEM medium (manufactured by Sigma) after adding palmitic acid (palmitic acid group), oleic acid (oleic acid group), EPA (EPA group), or DHA (DHA group) at 50 μM, or in the absence of the fatty acid (control group).

In the meanwhile, the Min6 cells cultured in the above (1-1) were incubated in the DMEM medium (manufactured by Sigma) for 48 hours as in the case of the above (1-2) but without adding the 0.4 mM palmitic acid (normal group), and these cells were washed twice with the PBS(−) and incubated in the DMEM medium (manufactured by Sigma) in the absence of the fatty acid in 5% $CO_2$ at 37° C. for another 48 hours as in the case of the control group of the above (1-3) to prepare the sample (normal group).

(2) Measurement of Insulin Secretion

Figure 2:
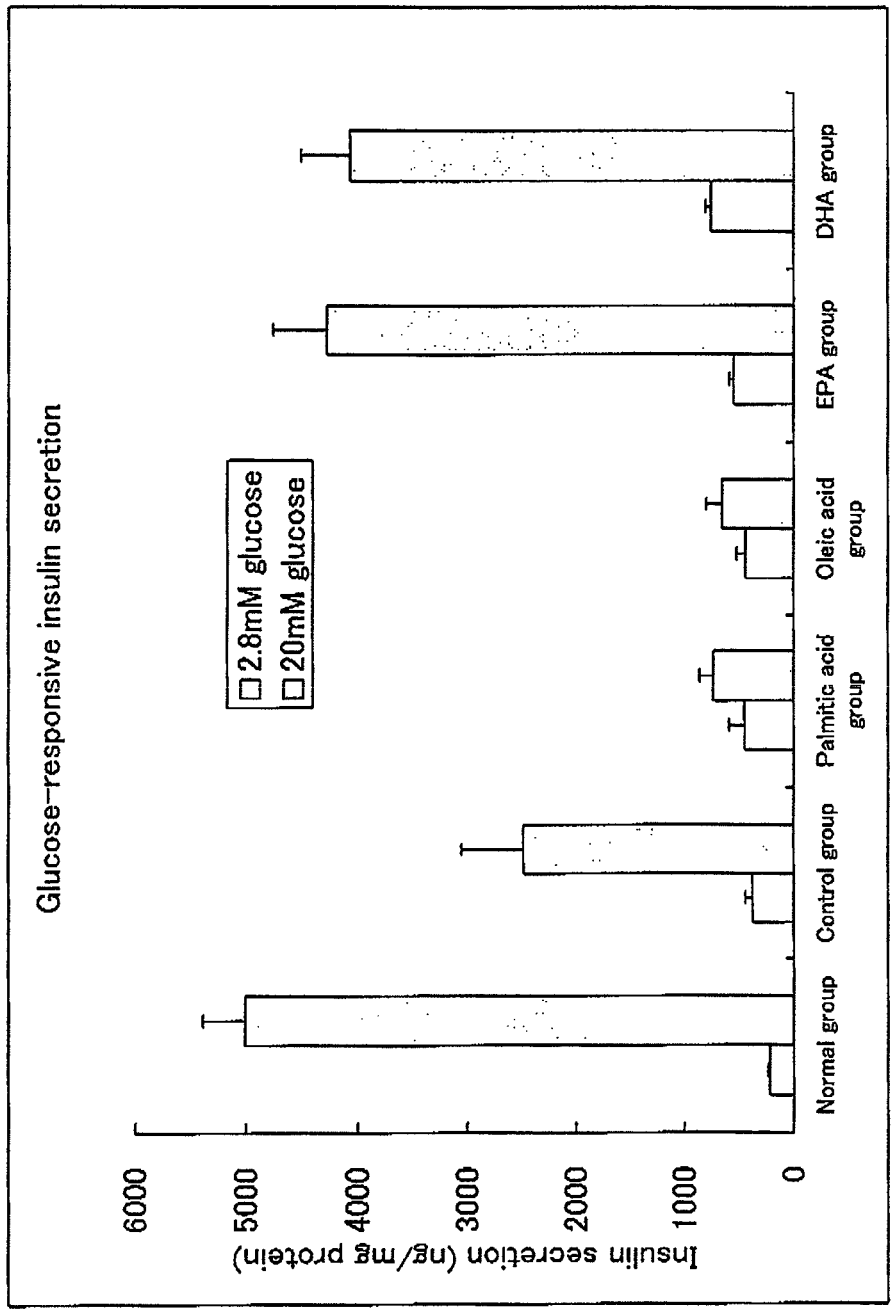
FIG. 2 is a graph showing the effect of the lipotoxicity relieving agent of the present invention in relieving the impaired insulin secretion of the pancreatic β-cell induced by the lipotoxicity. More specifically.

The stimulation with glucose was conducted by repeating the procedure of Experimental Example 1(2), and the sample that had been stimulated with 2.8 mM glucose and the sample that had been stimulated with 20 mM glucose were collected and the amount of insulin per mg of the protein were measured. The results are shown in FIG. 2.

The load of the 0.4 mM palmitic acid resulted in the decrease of the insulin secretion of the sample stimulated with 20 mM glucose from 5007 ng (normal group, assumed to be 100%) to 2481 ng (control group, 49.6%). The insulin secretion was 4278 ng (85.4%) in the EPA group and 4073 ng (81.4%) in the DHA group, while it was 742 ng (14.8%) in the palmitic acid group and 659 ng (13.2%) in the oleic acid.

As demonstrated by this result, while the palmitic acid and the oleic acid worsened the impaired insulin secretion induced by the lipotoxicity, the EPA and the DHA had the restorative effect on the impaired insulin secretion induced by lipotoxicity.

Experimental Example 3

Inhibitory Effect of the Long Chain Polyunsaturated Fatty Acid on the Increase of Blood Free Fatty Acid and the Impaired Insulin Secretion Induced by Lipotoxicity of the Pancreatic β-Cell in Palmitic Acid Fed Mice Male mice (C57BL/6J, 8 week old, purchased from Clea Japan, Inc.) were fed on fish meal free F1 (manufactured by Funabashi Farms Co., Ltd.) for 1 week, and the mice were divided into 4 groups each including 9 to 10 mice. The 4 groups of mice were freely fed for 28 days on (1) fish meal free F1 (control group), (2) fish meal free F1 containing 20% by weight of tripalmitic acid added (palmitic acid group), (3) F1 feed not containing any fish meal having 20% by weight of tripalmitic acid and 5% by weight of EPA-E added (the group of palmitic acid plus EPA), and (4) F1 feed not containing any fish meal having 5% by weight of EPA-E added (EPA group).

Figure 3:
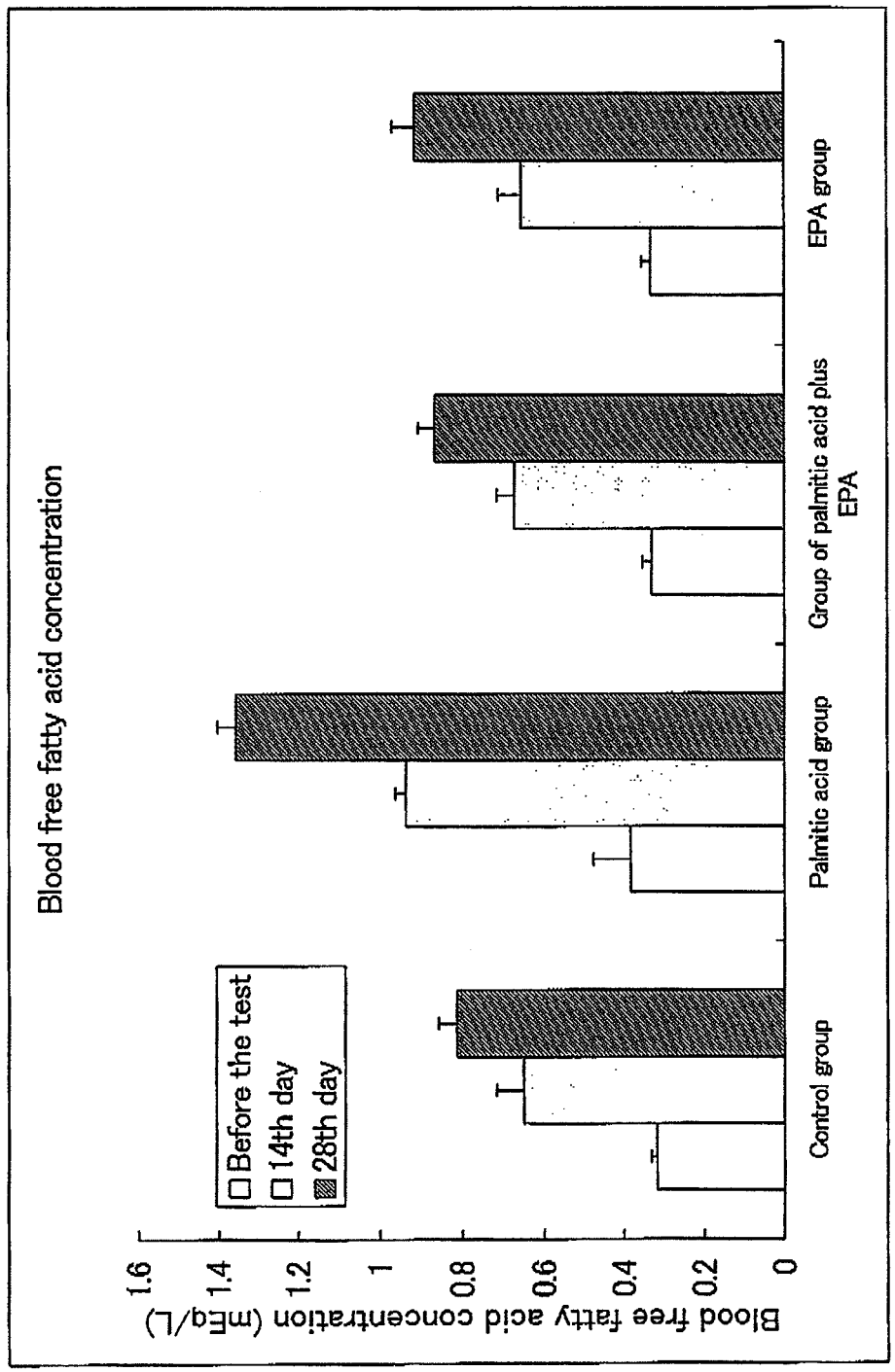
FIG. 3 is a graph showing blood free fatty acid concentration of the mice of various groups under the load of palmitin.

Before the start of the experiment, on 14th day, and on the final day, blood was taken from orbital venous plexus after fasting for 16 hours. The serum was separated, and blood free fatty acid was enzymatically measured by using NEFA Test Wako (Wako Pure Chemical Industries, Ltd.). The results are shown in FIG. 3. Langerhans' islet was isolated by way of density gradient method from the pancreas that had been treated with collagenase, and cultivated in 10% (v/v) fetal bovine serum (purchased from Iwai Chemicals Company) and RPM 11640 medium) supplemented with 1% by weight of penicillin streptomycin (manufactured by Sigma) in 5% $CO_2$ at 37° C. for 2 hours. The glucose-stimulated insulin secretion was then evaluated according to the procedure described in Experimental Example 1-(2). The results are shown in FIG. 4.

The Langerhans' islet was washed with PBS(−) and vigorously shaked in 20 μL of TNE buffer (0.1M Tris-HCl, pH 7.4, 2M NaCl, 10 mM EDTA) to prepare the cell lysate. 20 μL of this cell lysate was added to 100 μL of chromogenic solution (1.2 μL of Hoechst 33258 (manufactured by Wako Pure Chemical Industries, Ltd.) added to 1 mL of TNE buffer), and the reaction was allowed to proceed at room temperature for at least 8 hours, and the measurement was conducted by using an excitation wavelength of 350 nm and a measurement wavelength of 450 nm. Similar evaluation was conducted by using bovine thymus DNA (manufactured by Sigma) to prepare a calibration curve to thereby enable determination of the DNA amount. Amount of insulin per μg of the DNA of the Langerhans' islet was measured.

FIG. 3 shows effect of each fatty acid on the serum free fatty acid. As shown in FIG. 3, serum free fatty acid concentration increased more significantly with time in the palmitic acid group compared to the control group. The blood free fatty acid concentration of the EPA group and the group of palmitic acid plus EPA was similar to that of the control group. As demonstrated by this result, EPA has the effect of suppressing the increase of the plasma free fatty acid concentration in palmitic acid fed mice while EPA used alone does not affect the blood free fatty acid concentration.

Figure 4:
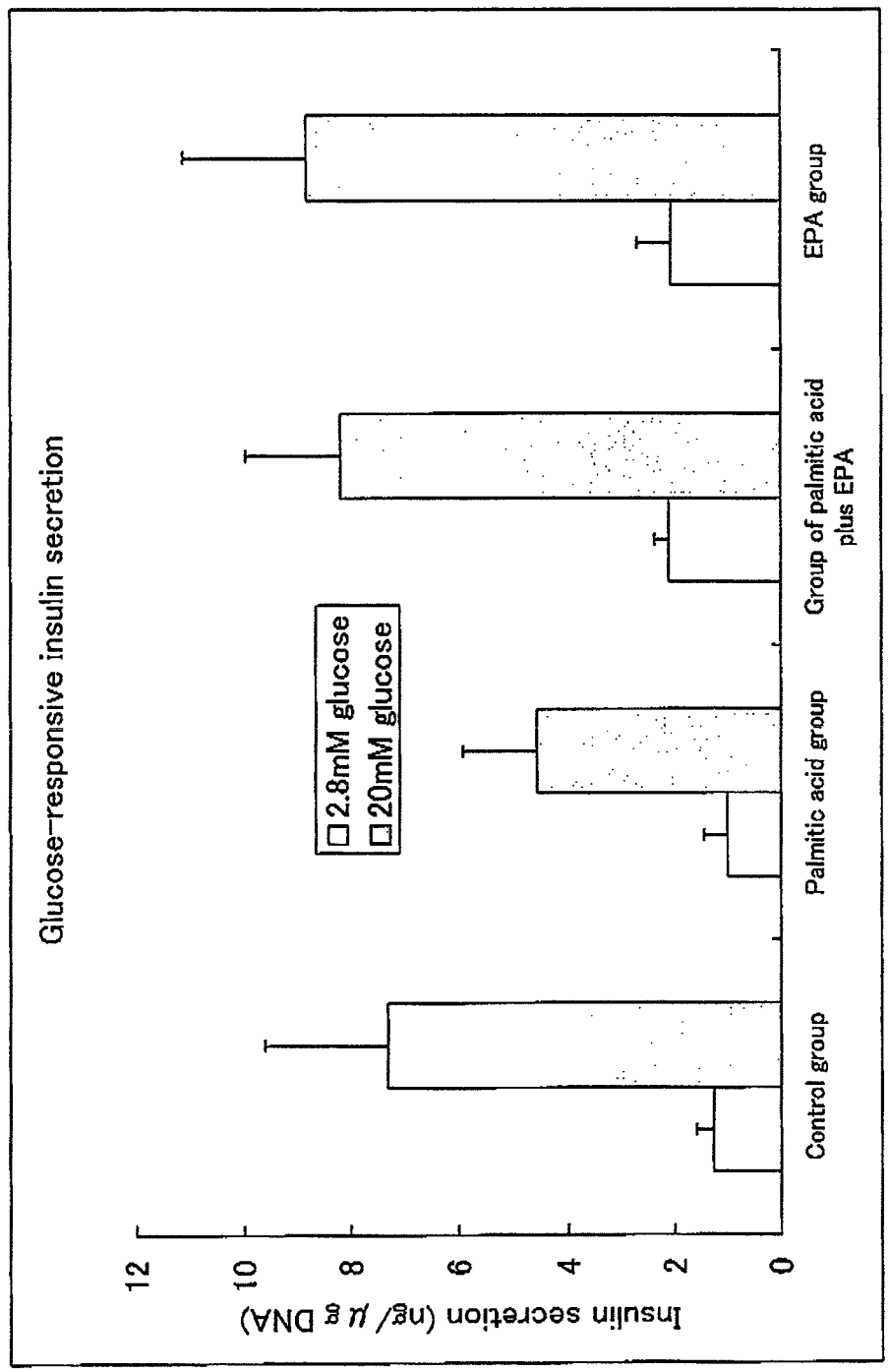
FIG. 4 is a graph showing insulin secretion per μg of the DNA when pancreatic β-cell separated from the mice of various groups under the load of palmitin is stimulated with glucose.

FIG. 4 shows the effect on the impaired insulin secretion.

No difference was recognized for the insulin secretion of the samples stimulated with 2.8 mM glucose between the groups. With regard to the insulin secretion of the samples stimulated with 20 mM glucose, the insulin secretion was 7.3 ng in the control group (assumed to be 100%) whereas it was reduced to the level of 4.6 ng (63%) in the palmitic acid group. The insulin secretion was 8.9 ng (121%) in the EPA group and 8.2 ng (111%) in the group of palmitic acid plus EPA. As demonstrated by this result, EPA has the effect of inhibition on the impaired insulin secretion induced by lipotoxicity while EPA used alone does not affect the insulin secretion.

Experimental Example 4

Figure 5:
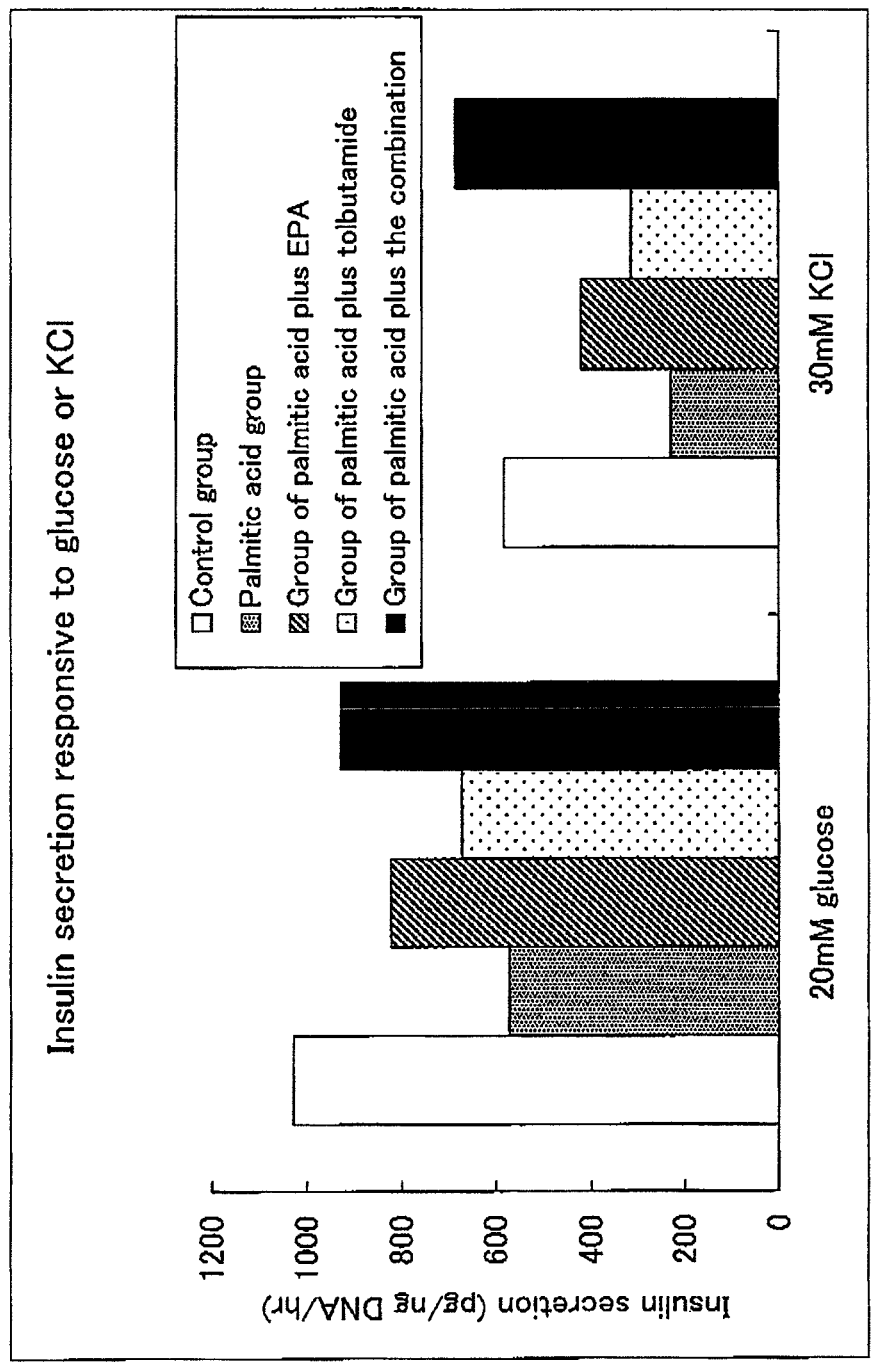
FIG. 5 is a graph showing the effects of the combined use of a long chain polyunsaturated fatty acid and an insulin secretion promoter on the impaired insulin secretion of the pancreatic β-cell induced by the lipotoxicity.

Effect of Combined Use of the Long Chain Polyunsaturated Fatty Acid and Insulin Secretion Promoting Agent on the Impaired Insulin Secretion of Pancreatic β-Cell Induced by Lipotoxicity Langerhans' islet was isolated from the pancreas of male mice (C57BL/6J, 8 week old, purchased from Clea Japan, Inc.) and cultured according to the procedure of Experimental Example 3, and effect of 50 μM EPA alone (the group of palmitic acid plus EPA), 5 mM tolbutamide alone (the group of palmitic acid plus tolbutamide), and combined use of 50M EPA and 5 mM tolbutamide (the group of palmitic acid plus the combination) on the suppression of the insulin secretion stimulated with 20 mM glucose and the insulin secretion stimulated with 30 mM KCl induced by 0.4 mM palmitic acid were measured according to the procedure of Experimental Example 1. Amount of insulin per 1 ng DNA of the Langerhans' islet was evaluated according to the procedure of Experimental Example 3. The results are shown in FIG. 5.

The insulin secretion of the sample stimulated with 20 mM glucose was 1029 pg in the control group (assumed to be 100%) whereas it decreased to 572 pg (55.6%) in the palmitic acid group. The insulin secretion was 823 pg (80.0%) in the group of palmitic acid plus EPA, 673 pg (65.4%) in the group of palmitic acid plus tolbutamide, and 928 pg (90.2%) in the group of palmitic acid plus the combination. The insulin secretion of the sample stimulated with 30 mM KCl was 583 pg in the control group (assumed to be 100%) whereas it was decreased to 229 pg (39.3%) in the palmitic acid group. The insulin secretion was 422 pg (72.4%) in the group of palmitic acid plus EPA, 316 pg (54.2%) in the group of palmitic acid plus tolbutamide, and 688 pg (118.0%) in the group of palmitic acid plus the combination.

As demonstrated by this result, EPA and tolbutamide have the effect of relieving the impaired insulin secretion induced by lipotoxicity when used alone, and such effect is enhanced when they are used in combination.

Next, some formulation embodiments of the lipotoxicity relieving agent of the present invention are described.

Example 1

Soft Capsules

A soft gelatin capsule (with the volume of about 0.5 mL) was sterilized. α-tocopherol was added to 0.2% by weight to an ethylated and purified fish oil, namely a composition containing 90.6% by weight of EPA-E, 2.3% by weight of ethyl arachidonate, 2.2% by weight of ethyl octadecatetraenoate, and 0.7% by weight of ω-3-ethyl icosatetraenoate. The capsule was filled with this composition so that 300 mg of EPA-E is in the capsule. The capsule was then sealed.

Example 2

Soft Capsules 10 kg of purified fish oil containing 28% of EPA and 0.1 kg of α-tocopherol were placed in a stirring tank, and the mixture was agitated until the mixture became homogeneous to prepare a liquid mixture of the starting materials. In the meanwhile, 2.6 kg of gelatin, 0.9 kg of glycerin, and 1.8 kg of water were mixed, and the mixture in the form of a film was injection molded in the shape of capsules (ellipsoid) each having an inner volume of 300 mg. These capsules were each filled with 300 mg of the liquid mixture of the starting materials and the injection port was heat sealed to thereby produce 33,600 capsules of EPA containing preparation. The capsule had a total weight of 460 mg, and EPA content per capsule was 18.1% by weight.

Example 3

Soft Capsules

Soft gelatin capsule (having an inner volume of about 1 mL) was sterilized, and this capsule was filled with a composition containing 1000 mg of ethylated and purified fish oil (containing 900 mg of polyunsaturated fatty acid ethyl ester (containing 465 mg of EPA-E and 375 mg of DHA-E)) and 4 mg of α-tocopherol. The capsule was then sealed.

Example 4

Microcapsules 0.2% by weight of α-tocopherol was added to an ethylated and purified fish oil, namely, a composition containing 90.6% by weight of EPA-E, 2.3% by weight of ethyl arachidonate, 2.2% by weight of ethyl octadecatetraenoate, and 0.7% by weight of ω-3-ethyl icosatetraenoate, and this oily mixture was placed in the tank for supplying the filling of an automatic soft capsule machine comprising two concentric cylinders. In the meanwhile, a coating solution separately prepared by mixing 37.8% by weight of gelatin, 9.4% by weight of glycerin, 5.7% by weight of D-sorbitol, and 47.2% by weight of purified water was placed in a tank for supplying the coating solution of the automatic soft capsule machine. After adjusting the speed of the oily mixture to be filled in the capsule moving through the inner nozzle of the capsule machine to 9.7 g/min, and the speed of the coating solution moving through the outer nozzle to 2.3 g/min, lower portion of the orifice was vibrated at 200 Hz, and spherical seamless microcapsules having a diameter of about mm, a coating percentage of 19%, and a weight of 3.1 mg were prepared while adjusting the speed of the cooling medium. These microcapsules were packaged by 410 mg in nitrogen gas atmosphere using a laminated aluminum foil (comprising moisture proof cellophane, an aluminum foil, and polyethylene) having a thickness of 0.2 mm.

The invention claimed is:

1. A method for treating a hyper-free fatty acidemia accompanied by impairment of glucose-stimulated insulin secretion of pancreatic β-cells comprising:
    administering to a patient in need thereof a therapeutically effective amount of a composition comprising, as an effective component, icosapentaenoic acid, docosahexaenoic acid, salts thereof, glyceride derivatives thereof, or ethyl ester derivatives thereof, wherein the concentration of a fatty acid in the patient's plasma is reduced after the composition is administered at 0.1 to 9 g/day in terms of icosapentaenoic acid and/or docosahexaenoic acid.

2. The method according to claim 1, wherein the patient suffers from an impaired cell death of pancreatic β-cells.

3. The method according to claim 1, wherein the patient continuously or repetitively exhibits a higher than normal concentration of a free fatty acid selected from palmitic acid, stearic acid or oleic acid in the free fatty acid in plasma prior to the administering step.

4. The method according to claim 1, wherein the patient continuously or repetitively exhibits a higher than normal proportion of palmitic acid, stearic acid or oleic acid, in the free fatty acid in plasma prior to the administering step.

5. The method according to claim 1, wherein the higher than normal concentration of the free fatty acid continues at least 48 hours prior to the administering step.

6. The method according to claim 1, wherein the higher than normal concentration of the free fatty acid continues at least 28 days prior to the administering step.

7. The method according to claim 1, wherein the patient has at least one of a pathological condition selected from the group consisting of obesity, overeating, abnormal glucose tolerance, hyperinsulinemia, diabetes, hepatic insufficiency, liver cirrhosis, hepatitis, renal failure, cardiac failure, and cardiomyopathy.

8. The method according to claim 1, wherein the composition comprises ethyl icosapentate and/or ethyl docosahexaenoate.

9. The method according to claim 1, wherein the content of the icosapentaenoic acid, docosahexaenoic acid, salts thereof, glyceride derivatives thereof, or ethyl ester derivatives thereof is 85% by weight or more in relation to the weight of total fatty acid content in the composition.

10. The method according to claim 1, wherein the content of the icosapentaenoic acid, docosahexaenoic acid, salts thereof, glyceride derivatives thereof, or ethyl ester derivatives thereof is 95% by weight or more in relation to the weight of total fatty acid content in the composition.

11. The method according to claim 1, wherein the icosapentaenoic acid, docosahexaenoic acid, salts thereof, glyceride derivatives thereof, or ethyl ester derivatives thereof is administered orally at 0.5 to 6 g/day in terms of icosapentaenoic acid (EPA).

12. The method according to claim 1, wherein the icosapentaenoic acid, docosahexaenoic acid, salts thereof, glyceride derivatives thereof, or ethyl ester derivatives thereof is administered orally at 1 to 3 g/day in terms of icosapentaenoic acid (EPA).

13. The method according to claim 1, wherein the composition is administered in combination with a sulfonylurea insulin secretion promoter.

14. The method according to claim 13, wherein the sulfonylurea insulin secretion promoter is at least one selected from the group consisting of tolbutamide, glimepiride, gliclazide and glibenclamide.

15. The method according to claim 1, wherein the composition is administered for at least 48 hours.

16. The method according to claim 1, wherein the composition is administered for at least 28 days.

17. The method according to claim 1, wherein the composition is administered to the patient while monitoring a concentration of at least one of palmitic acid, stearic acid and oleic acid in the patient's plasma.

* * * * *